United States Patent [19]
Florion et al.

[11] Patent Number: 5,804,705
[45] Date of Patent: Sep. 8, 1998

[54] METHOD AND APPARATUS FOR MONITORING AQUEOUS MEDIA USING ELECTROLOCATING AQUATIC ANIMALS

[75] Inventors: André Florion, Laxou; Denis Terver, Villiers-lès-Nancy; Didier Cretien, Nancy; Marielle Thomas, Sologne, all of France

[73] Assignee: Nancie—Centre International De L'Eau, Vandoeuvre, France

[21] Appl. No.: 648,156

[22] PCT Filed: Nov. 18, 1994

[86] PCT No.: PCT/FR94/01346

§ 371 Date: Jul. 11, 1996

§ 102(e) Date: Jul. 11, 1996

[87] PCT Pub. No.: WO95/14925

PCT Pub. Date: Jun. 1, 1995

[30] Foreign Application Priority Data

Nov. 23, 1993 [FR] France ................................... 93/14209

[51] Int. Cl.$^6$ ........................... G01N 33/00; A01K 63/00
[52] U.S. Cl. ........................................... 73/61.41; 119/224
[58] Field of Search ............................ 119/224; 73/61.41

[56] References Cited

U.S. PATENT DOCUMENTS

| | | | |
|---|---|---|---|
| 4,626,992 | 12/1986 | Greaves et al. | 128/630 |
| 4,723,511 | 2/1988 | Solman et al. | 119/224 |
| 5,140,855 | 8/1992 | Gruber | 73/61.41 |
| 5,176,824 | 1/1993 | Willinger et al. | 210/151 |
| 5,307,052 | 4/1994 | Harrison et al. | 340/573 |
| 5,322,035 | 6/1994 | Hawes et al. | 119/227 |

FOREIGN PATENT DOCUMENTS

P2906884.6-52  2/1983  Germany ....................... G01N 33/18

*Primary Examiner*—Michael Brock
*Assistant Examiner*—Jay L. Politzer
*Attorney, Agent, or Firm*—Weiser and Associates P.C.

[57] ABSTRACT

Aquatic animals that emit electrical signals are used to detect changes in the operating conditions of an aqueous medium (e.g., the presence of a pollutant). In one embodiment, the aquatic test animals are fishes of a species known as *Apteronotus albifrons*, whose electrical signals have frequency variations on the order of 0.1% under constant operating conditions; the temperature of the aqueous medium is stabilized to within 0.1° C.; each aquatic test animal is placed in a perforated refuge within a holding tank in which the aqueous medium flows in a vertical direction; and three or more aquatic test animals are used, wherein phases of nychthemeral activity of the aquatic test animals are artificially offset to achieve overlapping of the nychthemeral activity of the aquatic test animals. All of these combine to yield a highly sensitive and reliable system for real-time biological monitoring of physico-chemical parameters of an aqueous medium.

21 Claims, 4 Drawing Sheets

METHOD AND APPARATUS FOR MONITORING AQUEOUS MEDIA USING ELECTROLOCATING AQUATIC ANIMALS

BACKGROUND OF THE INVENTION

1. Field of the invention

The invention relates to a method and an installation for the real-time biological monitoring of physico-chemical parameters of aqueous media using electrical signals emitted by electrically generating aquatic animals.

2. Description of the Related Art.

There is already a device of this type described in the German patent document DE 2 906 884 and making it possible to monitor the quality of the water by means of an electric fish placed in an observation tank. The water of the tank is connected to an electrode for receiving the discharges from the fish which are amplified and recorded. An alarm is provided in the event that limits fixed beforehand are overstepped.

The device operates preferentially with electric fish of the low frequency irregularly pulsating type (*Gnathonems petersii* and *Mormyrus hasselquisti*) but also with a low frequency undulating species (*Gymnarchus niloticus*).

It is based on the continuous measurement of one or more parameters which are not clearly stated; either the strength (from 0 to 5 mA is spoken of), or the voltage of the signals (a digital voltmeter is spoken of), or the frequency (nychthemeral rhythms of discharges from the fish are spoken of) is involved. Since this last quantity is extremely variable for the fish considered, even in the absence of environmental disturbance(s), the exploitation of the method requires complex statistical processing of the discharges.

The device furthermore includes a system for waking the fish so as to preclude having to observe the diurnal rest periods during which its frequency of emission diminishes. This forced activity of the fish gives rise to measurement disturbances; moreover, it is bad for the fish and is therefore not acceptable.

SUMMARY OF THE INVENTION

The inventive idea consists in using high frequency undulating and/or regularly pulsating electric animals, measuring in particular the frequency of emission of the discharges as well as the strength and shape of their signals. Their particular feature is that they emit electrical signals whose characteristics are extremely stable over time when the environmental conditions are themselves stable.

According to a preferred but not limiting embodiment of the invention, a species of fishes known as *Apteronotus albifrons* is used as test animal.

*Apteronotus albifrons* emits an undulating signal of low amplitude (a few volts in contact with the fish, a few millivolts within the sensing electrodes) and having a frequency of around 1000 Hz, and which is extremely stable over time (variation of the order of 0.1%) when the environmental conditions are themselves stable. Moreover its signal, far from being sinusoidal, includes a wide spectrum of harmonics which can also be exploited for the bio-monitoring of physico-chemical parameters of aqueous media.

Thus, these tropical fishes continually deliver an electric current, which they modulate in strength, shape and frequency in accordance with various factors in the environment such as temperature, pH, oxygen, the presence of toxic substances, etc.

To summarize, we have as starting point the finding that in a stable environment the characteristics of the electrical signal are also stable, and as a result to exploit the fact that modifications in environmental factors bring about a variation in the characteristics of the electrical signal in terms:

of frequency: fall, rise, frequency peaks, etc.

of strength of the electrical signal, of shape of the signal, that is to say modification of the spectrum of harmonics.

Analysis of these three characteristics of the electrical signal as well as a possible study of the motor behavior of the test animal for example with a video system will provide the information exploited by the method and the installation according to the invention.

A first problem to be solved relates to the very marked dependence of the frequency of the fish on the temperature of the water of the tank.

It turns out to be difficult to determine accurately the responses of the fish following variations in physical or chemical factors in the environment such as for example pH and oxygen or the presence of hydrocarbons and other toxic substances, if the temperature of the water is not perfectly controlled.

The objective of the invention in order to solve this first problem is to stabilize the temperature of the water in the vicinity of the test animal so as to avoid the occurrence, under standard conditions (without any pollution), of abrupt variations in the frequency of the test animal of the order of a few Hertz within a short span of time (apart from the test animal's natural frequency peaks).

In fact, given the close dependence which exists between temperature and frequency, the temperature factor is preferably circumvented so as to be able to record and analyze at any moment a variation in one or more characteristics of the electrical signal of the test animal during an environmental disturbance.

Another problem to be solved relates to the frequency of the mains which may induce stray effects, this problem is solved inter alia by choosing a species, for example, the aforesaid species, which emits signals at high frequencies which are therefore sharply distinguishable from the frequency of the mains.

The main objectives of the invention are:

to design a system which can be used in closed circuit for example for experimental studies, or in open circuit for example for the real-time monitoring of surface water;

to set up a high-performance thermal regulation rig capable of maintaining the temperature of the water of the aquarium as constant as possible;

to set up a system making it possible to obtain good homogenization of the liquid to be monitored at holding tank level, that is to say to optimize:

the shape of the holding tank, its volume, the rate of replenishment of the water fed into the holding tank and whose quality it is wished to test, the system for conveying water into this tank;

for the detection of toxicity, possibly to insert a stirring tank into the installation for the purpose of homogenizing the medium;

to minimize the volume of water circulating upstream of the holding tank so that the response time of the test animal, placed in the presence of a possible pollutant, is as small as possible.

The cited problems are solved and the fixed objectives are achieved by virtue of the method according to the invention which uses the signals emitted by high frequency undulating and/or regularly pulsating electric animals and more particularly by *Apteronotus albifrons*.

The method according to the invention is characterized in that it includes successive steps of thermal stabilization of the sensed water, feeding of water into one or more holding tanks each containing a test animal, information processing together with correction of measurements as a function of at least one parameter influencing the signal and not coming under the heading of pollution or disturbance of the liquid to be monitored.

Furthermore, the method requires the prior establishing of an electrical identity map for the test animal in order to determine the bounds between which the various characteristics of the electrical signal vary as measured under standard conditions ( unpolluted medium).

Preferably, use will be made of fishes with an artificially offset phase of nychthemeral activity.

The invention also pertains to all the installations which implement the aforesaid method.

BRIEF DESCRIPTION OF THE DRAWINGS

The invention will be better understood with the aid of the description which follows, given with reference to the following appended figures.

DETAILED DESCRIPTION

Figure 1:
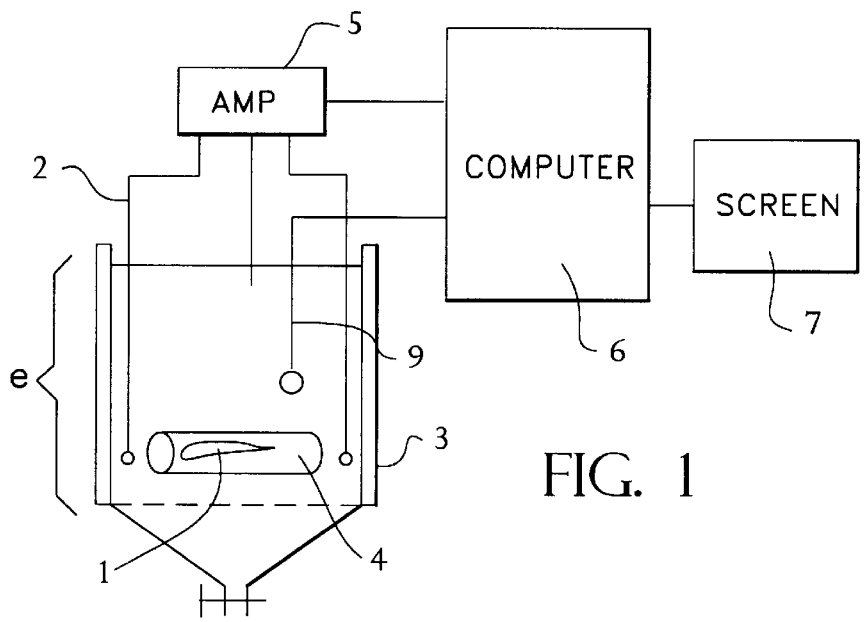
FIG. 1: basic diagram of the electrical and electronic circuit.

FIG. 1 is a basic diagram of the electrical and electronic circuit of the invention which includes the steps of sensing, processing of the sensed information, and exploitation of the data.

SENSING: The electrical information from *Apteronotus albifrons* (1) is gathered by at least two electrodes (2), made for example from stainless steel, dipping vertically into the mid-plane of the water of an aquarium (3). They determine a sensing channel which gathers the undulating variations of the electric field continually surrounding the test animal (1).

A thermal probe (9) detects the temperature of the bath.

Sensing of the electrical information is optimal when the test animal lies in the plane determined by the electrodes. This problem is solved by setting up a refuge (4) in the desired place, for example a PVC tube in which *Apteronotus albifrons* lodges, this species being accustomed in the wild to lodge in cavities or holes.

PROCESSING OF THE INFORMATION: The periodic variations thus collected by the electrodes are weak (a few millivolts). They are subjected to amplification for example by a preamplifier followed by a differential amplifier (5) (with three electrodes for example) which takes their value to 12 volts for example, without modifying their shape or their frequency.

COMPUTER EXPLOITATION OF THE ELECTRICAL SIGNAL by a microcomputer (6)

The recorded information relates to:

1. The frequency of the test animal: recording at defined time intervals (from a few hundredths of a second to a few seconds or minutes) of the number of electrical pulses per second.

2. The shape and strength of the electrical signal, in particular, study of the harmonics (Fourier analysis).

The software developed specifically for this study makes it possible to measure the frequency with an accuracy of $\frac{1}{10}$th of a Hertz. The measurements are generally made every second (option of working over time intervals larger or smaller than a second); the frequency is displayed in real time on a screen (7) and stored automatically in files (4 hours for measurements every second) over a practically unlimited period.

Moreover, the software makes it possible to display the shape of the signal in pseudo-real time (oscilloscope function). Every n seconds, an "image" file of the curve can be stored on a disc for Fourier analysis. Moreover, the temperature of the water of the aquarium in which the test animal is kept can be seen on the screen (7) and stored in real time (accuracy of the order of $\frac{1}{100}$th of a degree Celsius).

Figure 5:
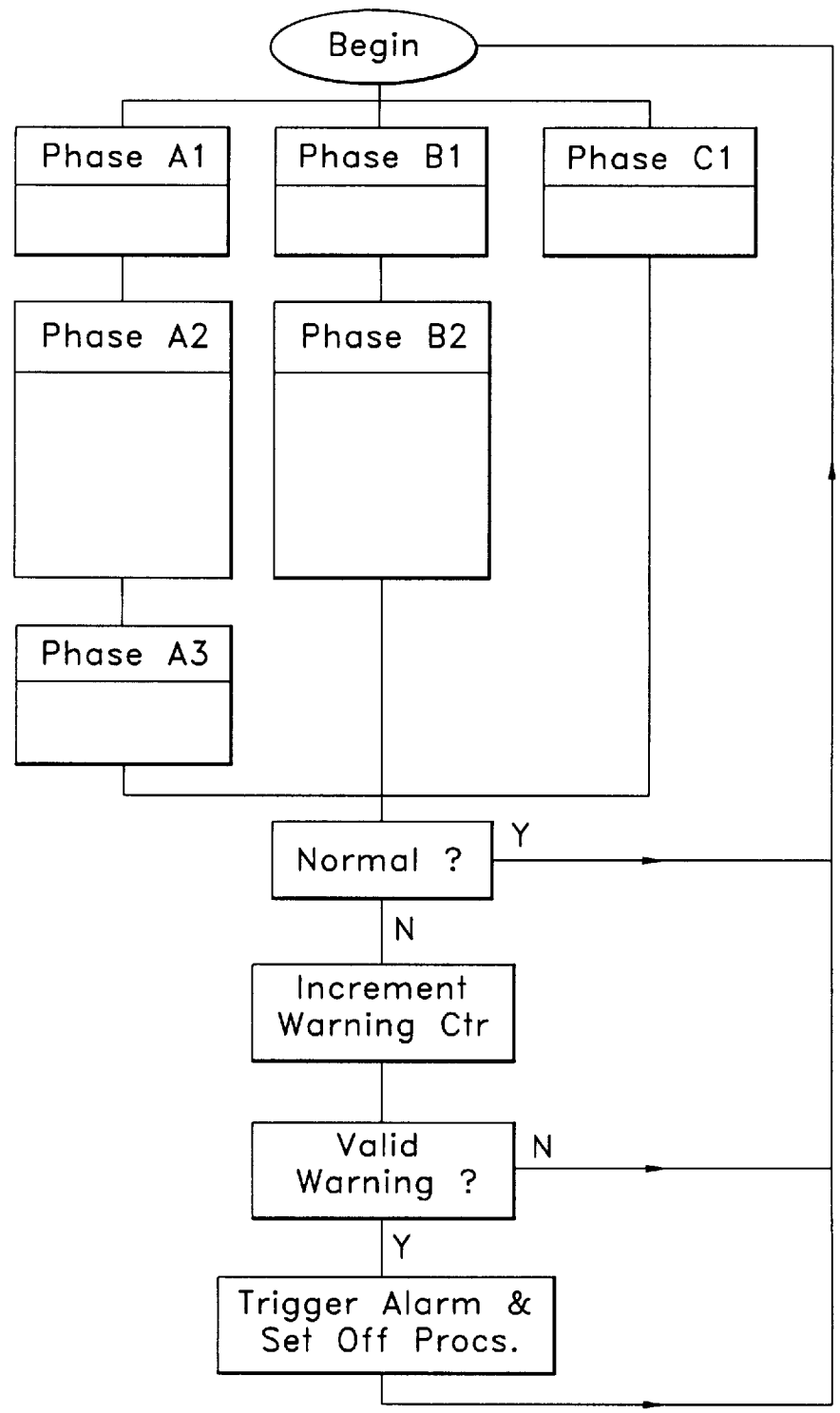
FIG. 5: overview of the processing program.

Analysis of the characteristics of the electrical signal: Computer analysis is carried out according to the program overviewed in FIG. 5 (given by way of nonlimiting example):

For each animal, an electrical identity map will be established beforehand in order to determine the bounds between which the various characteristics of the electrical signal vary under standard conditions (unpolluted medium).

The signals are processed in parallel along three routes A, B, C (see FIG. 5) which break down as follows:

phase A1: measurement of the frequency, phase A2: correction of the measurement as a function of the parameters measured in phase C1, phase A3: comparison with the sliding mean of the last "n" measurements, phase B1: sensing of the shape of the signal and spectral analysis, phase B2: comparison with the electrical "identity map" for the test animal as a function of the parameters measured in phase C1, phase C1: measurement of the temperature and possibly of other parameters influencing the signal and not coming under the heading of pollution.

Through a conventional system of comparison, if the measurements are normal, or if a warning is not substantiated, the program is reinitialized. If the warning is substantiated an alarm is triggered and sets off procedures which vary depending on the origin of the warning.

Various monitoring and alarm triggering means can be implemented such as: remote monitoring, remote action, video.

Figure 2:
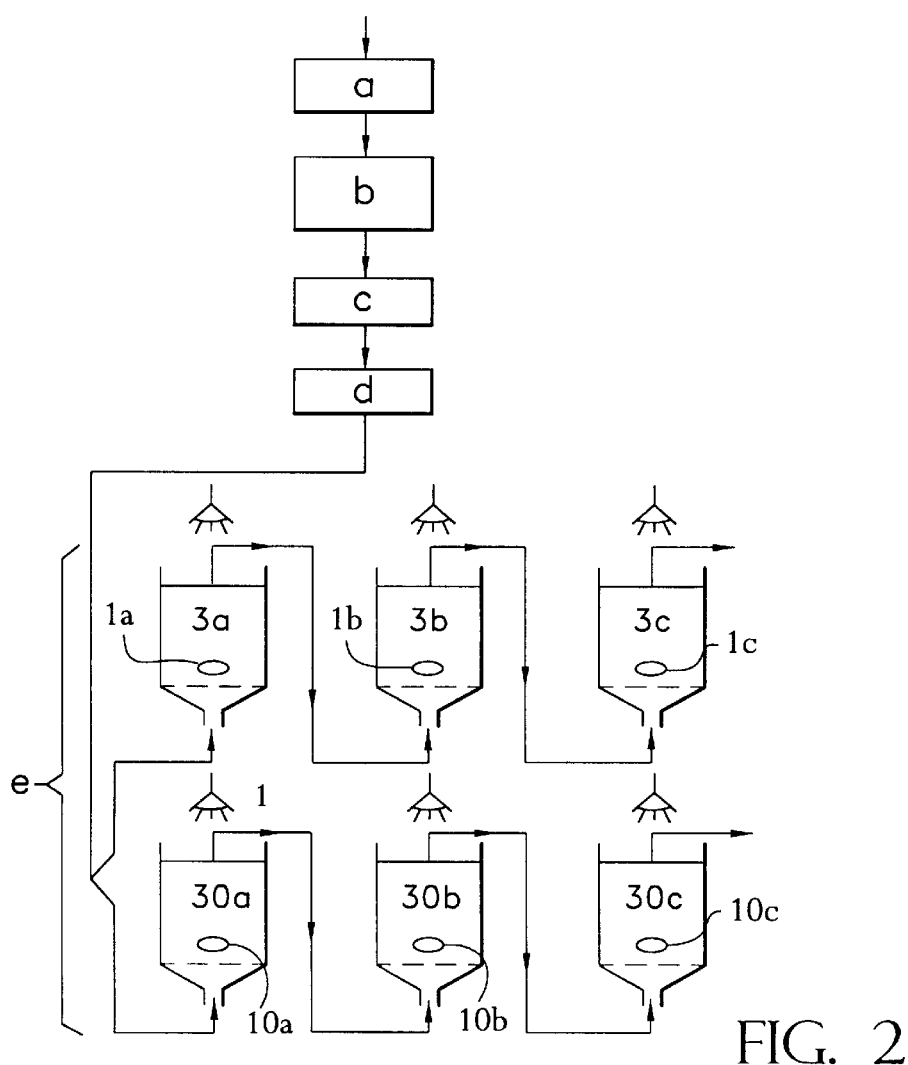
FIG. 2: basic diagram of a first variant of the hydraulic circuit.

FIG. 2 is a basic diagram of the hydraulic and thermal regulation circuit for implementing the invention. The following main steps are evident:

a) continual sampling of the liquid whose quality it is wished to test, by means of a pump with a regular flow rate so as to replenish the medium correctly.

b) depending on the situation, a possible step for removing particles in suspension. This will be carried out for example by a filtration system or for example by layered settling; a step of stirring the liquid to be monitored can also be interposed.

c) coarse preheating of the liquid with a thermal regulator operating in on/off mode, d) very accurate heating of the liquid to the temperature suitable for the test animal (1) (i.e. 26°–27° C.). This is carried out by means of a very accurate thermal regulation unit including a high-performance regulator, driving a controller (thyristor-based power unit) and of a Pt 100 type platinum probe located at the output of the reheater, that is to say in the pipe between the heating tank and the holding tank. The regulator sends the dimmer a signal which can vary between 0 and 20 mA corresponding to variable regulation of the power of the resistors. This thermal regulating unit enables liquid to be conveyed into the holding tank (3) at a very stable temperature (with variation less than 0.1° C.) despite the thermal disparities of the liquid sampled at the start.

It is important to note the need for liquid to be supplied at an extremely constant temperature to the holding tank, given the close correlation which exists between this factor and the frequency of discharges of *Apteronotus albifrons*. In fact, depending on the individual we shall record a variation of 40 to 45 Hz per degree Celsius, these two quantities varying in the same direction.

e) feeding of the thermally regulated liquid into one or more lagged holding tanks (3). The thermally regulated liquid is fed to the base of the cylindricoconical shaped holding tank (3) and is removed by a recovery device at the surface. The test animal (1) is therefore subjected to a vertical current of liquid. A cylindrico-conical shape is preferable to a parallele-pipedal shape for homogeneous feeding of the liquid over the whole cross section of the tank.

In order to circumvent the individual variations among test animals, we shall record the electrical and behavioral responses simultaneously for several animals, for example three animals (1a, 1b, 1c). Additionally, the thermally regulated liquid will be distributed among three cylindrico-conical units (3a, 3b, 3c). We envisage perhaps a system of tanks, that is to say a device comprising two or more groups of three tanks. In fact, for the test animal used here certain electrical information is more easily gathered during the diurnal phase (corresponding to the rest phase of the fish). Additionally, the idea of using two or even three animals, so that there is always one in the illuminated phase, will perhaps constitute a beneficial recourse for continuous monitoring of the quality of the water. The measurements will then be made on the animal or animals in the illuminated phase.

Represented in FIG. 2 is a system with relay animals including two units of three tanks (3a, 3b, 3c) and (30a, 30b, 30c) and two groups of three test animals (1a, 1b, 1c) and (10a, 10b, 10c) whose diurnal and nocturnal phases are artificially offset by twelve hours, the measurements being made on the group in its diurnal phase, here the group (1a, 1b, 1c), the group being in its nocturnal phase.

Figure 3:
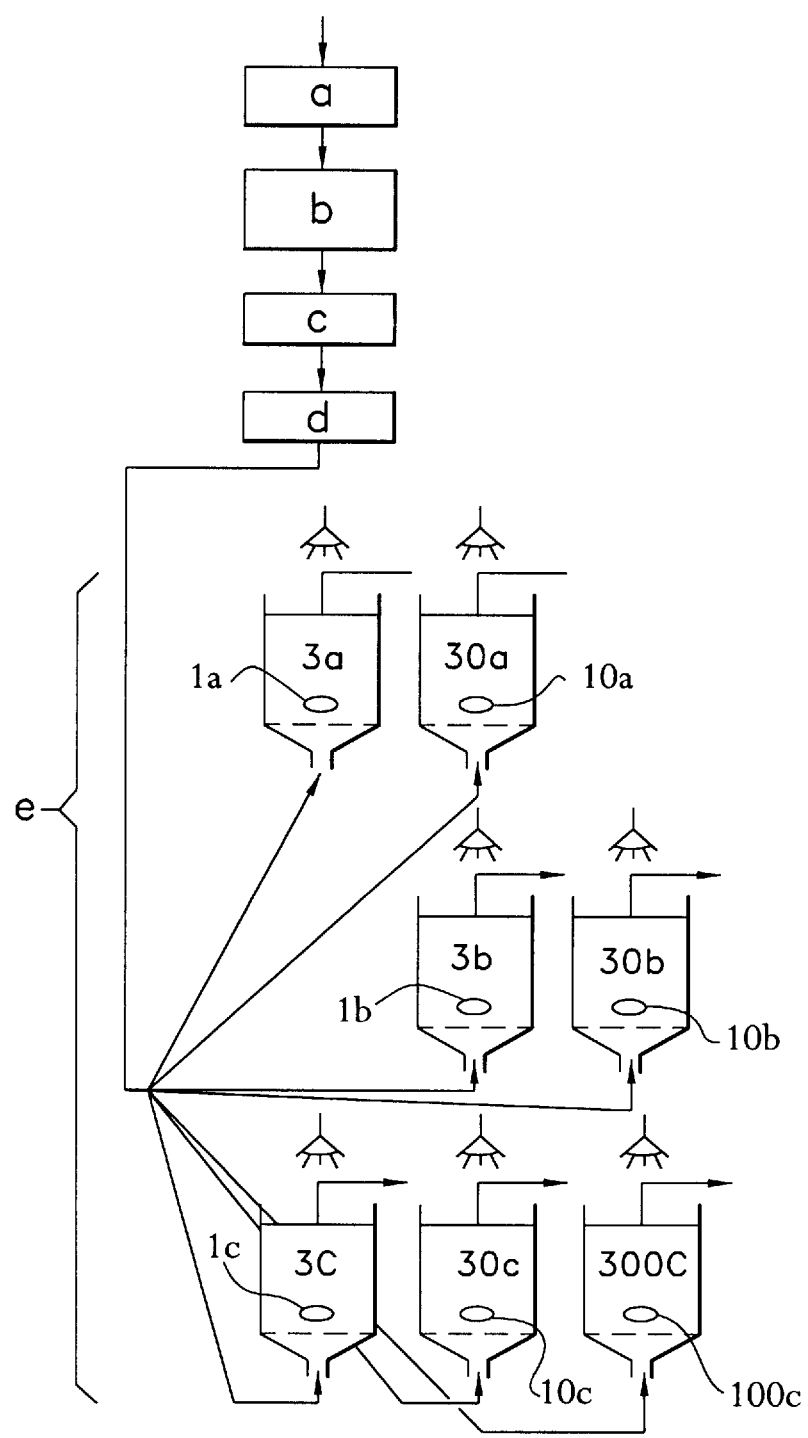
FIG. 3: basic principle of a second variant of the hydraulic circuit.

By way of example, FIG. 3 shows two units of tanks (3a, 30a) and (3b, 30b) each including two fish (1a, 10a,) and (1b, 10b) mutually offset by twelve hours and a unit of tanks (3c, 30c, 300c) including three fish (1c, 10c, 100c) offset over time with overlap periods of four hours, each fish having twelve hours of daytime and twelve hours of nighttime.

Of course, the numbers of units of tanks, or of tanks in a unit, or the number of hours of offset or of overlap of the nychthemeral activities are chosen as a function of the application considered.

The tanks can be supplied in parallel (FIGS. 3, 4) or in series (FIG. 2), in all cases the liquid preferably is introduced into the bottom part of the tank and is removed at the top part so as to force the low-solubility pollutants which form a surface film, such as hydrocarbons, to cross the refuges (4).

Figure 4:
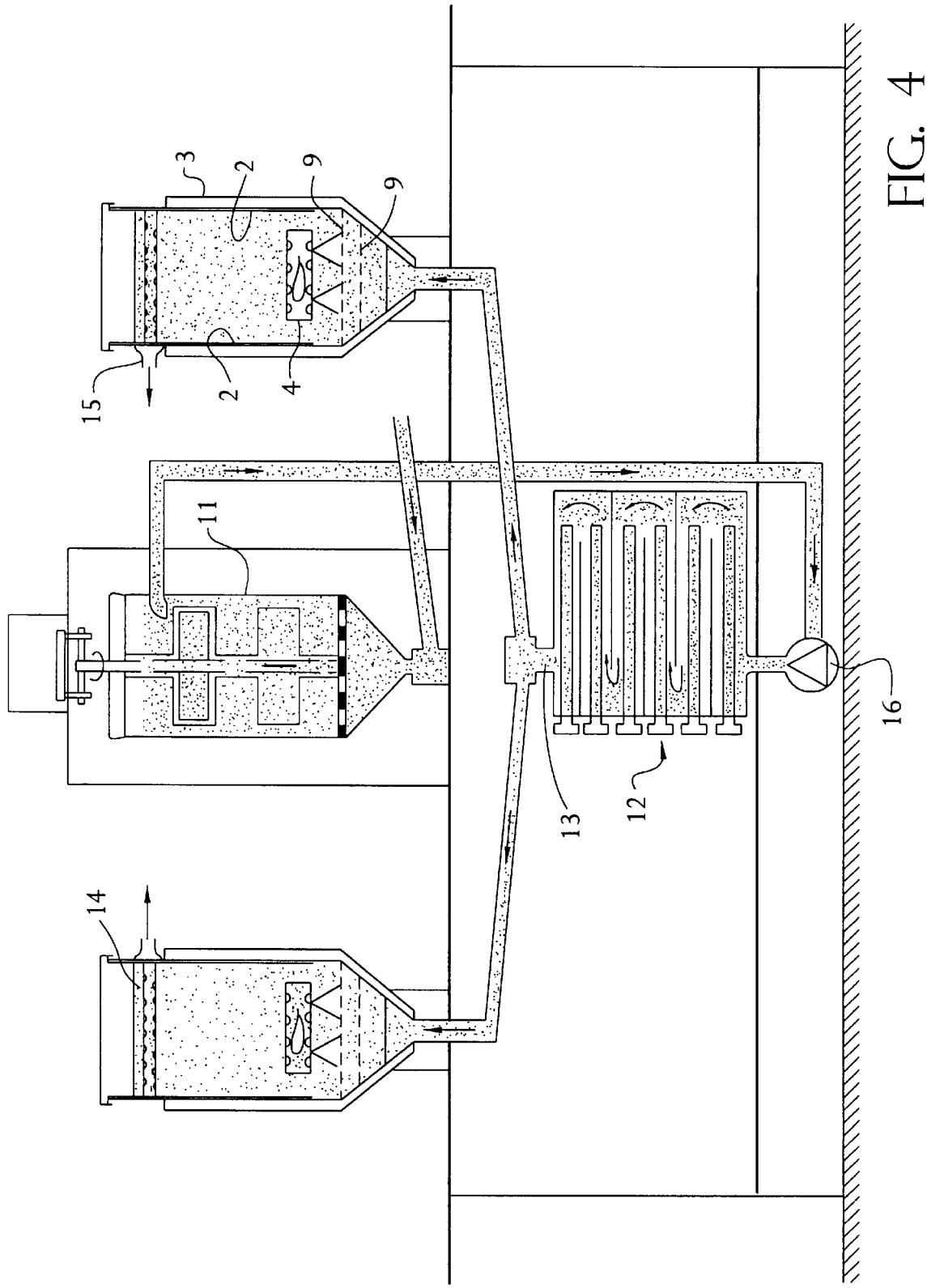
FIG. 4: diagram of an on-site installation of a surface water pollution monitoring station.

FIG. 4 shows by way of nonlimiting example an installation for implementing the invention in open circuit. The surface water sampled from the site to be monitored is dispatched after pumping and filtering to the bottom part of a conventional paddle stirring tank (11) provided upstream of a heating tank (12) in order to homogenize the medium.

The heating tank (12) includes a plurality of resistors arranged for example horizontally and staggered.

The water is brought to a constant temperature appropriate to the life of tropical fish (between 25° and 28°) from a sampling liquid temperature which varies greatly depending on the season.

The probe which drives the thermal regulator (13) records the temperature of the water at the exit of the heating tank.

The thermally regulated liquid is here dispatched into two units of several holding tanks (only two of which are represented), supplied in parallel and arranged in a circle around the stirring tank (11).

Each of the tanks here has a circular cross section but this shape is not limiting (it could for example be elliptical depending on the quality of sensing of the signal).

The bottom of a tank (3) includes a plurality of perforated plates (9) for homogenizing the flow within the tank, a refuge (4) in the form of a perforated tube whose perforations make it possible on the one hand to let through the vertical flow and on the other hand to observe the fish, a liquid sampling device (14) at the surface together with a pipe (15) for discharging into the monitored site. The electrodes (2) are placed vertically near the walls of the tanks (3) and in the longitudinal plane of symmetry of the tube (4) for optimal signal sensing.

A pump (16) affords a constant flow rate. The control, monitoring, electrical and/or audible and/or visual alarm systems are not represented in the figures.

There may be added thereto depending on the requirements:

- a video monitoring device, a behavioral modification of the fish being able to constitute a warning (for example if the test animal is gulping at the surface),
- a device for automatically sampling specimens of liquid for analyses, in the event of a warning,
- a "clear water" device for saving the fish in the event of pollution by cutting off the hydraulic circuit and automatically diverting to an unpolluted water circuit,
- a unit for monitoring various physico-chemical parameters (such as pH, oxygen, turbidity, conductivity, ammonia, etc . . . ) via specific physico-chemical sensors and returning the information collected to the computer,
- the performance features and advantages of the invention are numerous and are in particular:
  - its accuracy,
  - its speed (study of sublethal responses),
  - its sensitivity,
  - its reliability,
  - its ease of implementation,
  - its adaptability to various applications,
  - a very complete approach to the characteristics of the medium to be monitored (biological, physical and chemical approach),
  - its ability to detect continuously and in real time.

The field of application of the method or of an installation according to the invention is not limited to the monitoring of surface water with a view to detecting the appearance of pollution, but it can be extended to:

- the monitoring and/or control of all aqueous media in varied industrial fields (for example in pharmaceutical laboratories for monitoring the concentration stability of a substance)

the detection and/or measurement and/or regulation of temperature or of temperature variations requiring much greater accuracy than that of the currently known apparatuses, and this within any industrial field (accuracy of the fish of the order of a thousandth of a degree).

Finally, generally speaking the invention is not limited to the use of *Apteronotus albifrons* since any high frequency undulating and/or regularly pulsating aquatic animal may be suitable.

We claim:

1. A method for real-time biological monitoring of physico-chemical parameters of an aqueous medium using electrical signals emitted by one or more aquatic test animals that, under constant operating conditions, emit electrical signals having frequency variations of an order of about 0.1%.

2. The invention of claim 1, wherein the frequency of the electrical signals is distinguishable from the frequency of electrical signals generated by mains.

3. The invention of claim 1, wherein the frequency of the electrical signals is around 1000 Hz.

4. The invention of claim 1, wherein the aquatic test animals are fishes of a species known as *Apteronotus albifrons*.

5. The invention of claim 1, wherein the temperature of the aqueous medium is stabilized to within 0.1° C.

6. The invention of claim 1, wherein each aquatic test animal is placed in a perforated refuge within a holding tank in which the aqueous medium flows in a vertical direction.

7. The invention of claim 1, wherein three or more aquatic test animals are used, wherein phases of nychthemeral activity of the aquatic test animals are artificially offset to achieve overlapping of the nychthemeral activity of the aquatic test animals.

8. The invention of claim 1, wherein:
   the aquatic test animals are fishes of a species known as *Apteronotus albifrons*;
   the temperature of the aqueous medium is stabilized to within 0.1° C.; and
   each aquatic test animal is placed in a perforated refuge within a holding tank in which the aqueous medium flows in a vertical direction.

9. The invention of claim 8, wherein three or more aquatic test animals are used, wherein phases of nychthemeral activity of the aquatic test animals are artificially offset to achieve overlapping of the nychthemeral activity of the aquatic test animals.

10. A method for real-time biological monitoring of physico-chemical parameters of an aqueous medium using electrical signals emitted by one or more aquatic test animals, wherein the temperature of the aqueous medium is stabilized to within 0.1° C., wherein the aquatic test animals are fishes of a species known as *Apteronotus albifrons*.

11. The invention of claim 10, wherein each aquatic test animal is placed in a perforated refuge within a holding tank in which the aqueous medium flows in a vertical direction.

12. The invention of claim 10, wherein three or more aquatic test animals are used, wherein phases of nychthemeral activity of the aquatic test animals are artificially offset to achieve overlapping of the nychthemeral activity of the aquatic test animals.

13. A method for real-time biological monitoring of physico-chemical parameters of an aqueous medium using electrical signals emitted by one or more aquatic test animals, wherein each aquatic test animal is placed in a perforated refuge within a holding tank in which the aqueous medium flows in an upwelling vertical direction.

14. The invention of claim 13, wherein the aquatic test animals are fishes of a species known as *Apteronotus albifrons*.

15. The invention of claim 13, wherein three or more aquatic test animals are used, wherein phases of nychthemeral activity of the aquatic test animals are artificially offset to achieve overlapping of the nychthemeral activity of the aquatic test animals.

16. An apparatus for real-time biological monitoring of physico-chemical parameters of an aqueous medium using electrical signals emitted by one or more aquatic test animals, comprising:
   one or more holding tanks in which the aqueous medium flows in an upwelling vertical direction;
   a perforated refuge within each holding tank adapted to receive one of the aquatic test animals; and
   one or more electrodes within each holding tank for recording the electrical signals emitted by the aquatic test animal.

17. The invention of claim 16, further comprising means for stabilizing the temperature of the aqueous medium to within 0.1° C.

18. The invention of claim 16, comprising three or more holding tanks and means for artificially offsetting phases of nychthemeral activity of three aquatic test animals placed within the holding tanks to achieve overlapping of the nychthemeral activity of the aquatic test animals.

19. The invention of claim 16, wherein each holding tank has a conical bottom portion and a top portion having a circular or elliptical cross section, such that the aqueous medium is fed up from the conical bottom portion to the top portion.

20. The invention of claim 19, wherein each holding tank has one or more perforated plates for homogenizing the flow within the holding tank.

21. A method for real-time biological monitoring of physico-chemical parameters of an aqueous medium using electrical signals emitted by three or more aquatic test animals, wherein phases of nychthemeral activity of the aquatic test animals are artificially offset to achieve overlapping of the nychthemeral activity of the aquatic test animals, wherein the aquatic test animals are fishes of a species known as *Apteronotus albifrons*.

* * * * *